United States Patent [19]

Becker et al.

[11] Patent Number: 4,877,891

[45] Date of Patent: Oct. 31, 1989

[54] 1,1-DIALKOXY- OR 1,1-(ALPHA, OMEGA-METHYLENEDIOXY)-NON-2-YN-9-01 AND THEIR OH-PROTECTED DERIVATIVES

[75] Inventors: Rainer Becker, Bad Durkheim; Walter Seufert, Speyer; Ernst Buschmann; Christiane Brüchner, both of Ludwigshafen, all of Fed. Rep. of Germany

[73] Assignee: BASF Aktiengesellschaft, Ludwigshafen, Fed. Rep. of Germany

[21] Appl. No.: 228,681

[22] Filed: Aug. 5, 1988

[30] Foreign Application Priority Data

Aug. 8, 1987 [DE] Fed. Rep. of Germany ....... 3726511

[51] Int. Cl.$^4$ .................. C07D 309/10; C07C 43/303
[52] U.S. Cl. .................................... 549/416; 549/375; 549/374; 549/453; 549/347; 549/454; 549/214; 568/597; 560/113; 560/262; 556/446
[58] Field of Search ............... 549/453, 374, 375, 347, 549/454, 214, 416; 568/597; 560/113, 262; 556/446

[56] References Cited

U.S. PATENT DOCUMENTS 3,845,108  10/1974  Roelofs et al. ................. 260/488 H

FOREIGN PATENT DOCUMENTS 2098609A  11/1982  United Kingdom .

Primary Examiner—Nicky Chan
Attorney, Agent, or Firm—Oblon, Spivak, McClelland, Maier & Neustadt

[57] ABSTRACT 1,1-dialkoxy- or 1,1-($\alpha,\omega$-methylenedioxy)-non-2-yn-9-ol and their OH-protected derivatives of the general formula I

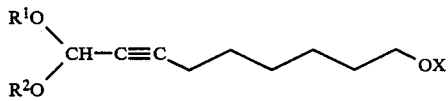

where $R^1$ and $R^2$ are each $C_1$–$C_6$-alkyl or together form an alkylene chain of 2 to 5 carbon atoms and X is hydrogen or a protective group which can be eliminated, their preparation and their use as intermediates.

1 Claim, No Drawings

1,1-DIALKOXY- OR 1,1-(ALPHA, OMEGA-METHYLENEDIOXY)-NON-2-YN-9-OL AND THEIR OH-PROTECTED DERIVATIVES

We have found that 1,1-dialkoxy- or 1,1-($\alpha,\omega$-methylenedioxy)-non-2-yn-9-ol and their OH-protected derivatives of the general formula I

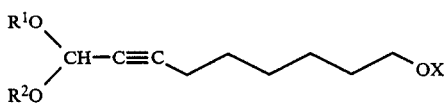

where $R^1$ and $R^2$ are each $C_1$–$C_6$-alkyl or together form an alkylene chain of 2 to 5 carbon atoms and X is hydrogen or a protective group which can be eliminated, are suitable as intermediates for the synthesis of E-7, Z-9-dodecadienyl acetate, the pheromone of the grape-berry moth (*Lobesia botrana*). This active ingredient was described for the first time in 1973 [Mitteilungen der schweizerischen entomologischen Gesellschaft 46 (1973), 71–73, US-A-3 845 108 and DE-A-24 40 759]. The preparation process, also described there, has 10, generally complicated, process steps and is thus very inconvenient; it is unsuitable for the synthesis of large amounts, as required for the use of pheromone active ingredients over large areas for insect control by the confusion method.

Because of the advantages of biological pest control with pheromones (very specific active ingredients which do not harm useful insects, no signs of resistance, good biodegradability, extremely low toxicity), a synthesis which is economical on an industrial scale is urgently required.

It is an object of the present invention to provide a technically simple preparation process for the pheromone active ingredient. We have found that this object is achieved by providing the novel compounds 1,1-dialkoxy- or 1,1-($\alpha,\omega$-methylenedioxy)-non-2-yn-9-ol and their OH-protected derivatives (I)

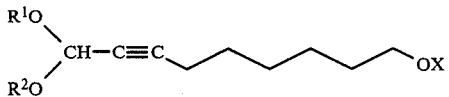

as intermediates, these compounds being readily available and, after hydrogenation and hydrolysis, giving the known substituted nonenals (III)

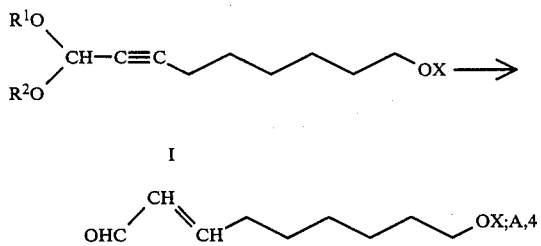

The use of the compounds of the nonenals (III) for the synthesis of the desired pheromone active ingredient has been described (GB-A-2 098 609 and Leibigs Ann. Chem. (1981), 1705).

In the nonynol derivatives I defined at the outset, $R^1$ and $R^2$ are each preferably straight-chain or branched low molecular weight alkyl, eg. methyl, ethyl, propyl, isopropyl, butyl, isobutyl, sec-butyl, pentyl or hexyl. Ethyl and methyl radicals are particularly preferred, since these compounds are particularly readily obtainable. $R^1$ and $R^2$ may furthermore be bonded to one another to form a 5-membered to 8-membered ring. In this case, 5-membered or 6-membered rings are particularly suitable, for example the 1,3-dioxane or 1,3-dioxolane system.

The novel derivatives of the non-2-yn-9-ol I can be prepared by reacting the known acetylene derivatives of type II

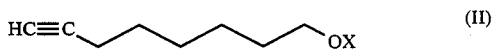

[J. Chem. Soc., Chem. Commun. 1973, 874)] with an orthoformate in the presence of, or after the action of, a strong base, for example an alkali metal amide, or a Grignard compound. Examples of alkali metal amides are lithium amide and potassium amide ($LiNH_2$, $NaNH_2$) and substituted amides, such as lithium diisopropylamide. Grignard compounds are alkylmagnesium chlorides, bromides or iodides, such as methylmagnesium bromide, ethylmagnesium chloride or methylmagnesium iodide.

The amount of base is not particularly critical; in general, a stoichiometric amount or a slight excess, for example an excess of from 10 to 20 mol %, based on the acetylene derivative I, is used. Larger excesses are possible but are not as a rule necessary.

The reaction is carried out at from 50° to 150° C. under atmospheric pressure or, if required, under autogenous or superatmospheric pressure of from 1.01 to 10 bar, in a suitable aprotic solvent, such as diethyl ether, methyl tert-butyl ether, tetrahydrofuran, dioxane or a glycol ether.

The ortho-esters advantageously used are commercial trimethyl orthoformate and triethyl orthoformate. The asymmetrically substituted and cyclic acetals I can be obtained by using the corresponding orthoformates which are known per se or can be prepared by well known methods, or can be synthesized from symmetric acyclic substituted acetals I by the well known method of transacetalization. The ortho-ester is used in general in an equimolar amount or a slight excess or in slightly less than the stoichiometric amount, based on the acetylene derivative I.

Suitable protective groups X which can be eliminated are hydroxyl protective groups which are stable to bases, for example $C_4$–$C_{20}$-tert-alkyl, preferably $C_4$–$C_{20}$-tert-alkyl which carries a tertiary carbon atom in the 1-position, such as tert-butyl, 1,1-dimethylprop-1-yl, 1,1-dimethylbut-1-yl, 1,1,2-trimethylprop-1-yl, 1,1-dimethylpent-1-yl, 1,1,2-trimethylbut-1-yl, 1,1,3-trimethylbut-1-yl, 1-ethyl-1-methylbut-1-yl, 1,1-dimethylhex-1-yl and 1,1-dimethyl-2-ethylbut-1-yl; $C_3$–$C_{20}$-trialkylsilyl, preferably $C_3$–$C_8$-trialkylsilyl, such as trimethylsilyl, triethylsilyl, tri-n-propylsilyl, triisopropylsilyl, tri-n-butylsilyl, dimethylethylsilyl, diethylmethylsilyl, dimethyl-n-propylsilyl, dimethylisopropylsilyl, dimethyl-n-butylsilyl and dimethyl-tert-butylsilyl; benzyl; acyls, for example alkanoyls, such as acetyl, propionyl and butyryl; benzoyl; acyclic acetal groups, for example $C_2$-$C_{20}$-alkoxymethoxy, preferably $C_2$-$C_9$-alkoxymethoxy, such as methoxymethoxy, ethoxymethoxy, n-propoxymethoxy, isopropoxymethoxy, n-butoxymethoxy, isobutoxymethoxy, sec-butoxymethoxy, tert-butoxymethoxy, n-hexyloxymethoxy and n-octyloxymethoxy; $C_3$-$C_{20}$-1-alkoxyethoxy, preferably $C_3$-$C_{10}$-1-alkoxyethoxy, such as 1-methoxyethoxy, 1-ethoxyethoxy, 1-n-propoxyethoxy, 1-isopropoxyethoxy, 1-n-butoxyethoxy, 1-isobutoxyethoxy, 1-sec-butoxyethoxy, 1-tert-butoxyethoxy, 1-n-hexyloxyethoxy and 1-n-octyloxyethoxy; and cyclic acetal groups, such as 2-furanyl, 2-tetrahydrofuranyl, 2-pyranyl, 2-tetrahydropyranyl, 1,3-dioxan-2-yl, 1,3-dioxan-4-yl and 1,4-dioxan-2-yl.

Elimination of the protective group for the preparation of the compounds I where X is hydrogen can be carried out in a conventional manner, for example by acid hydrolysis.

Preparation Examples

EXAMPLE 1

(a) 364 g (2.0 moles) of 8-tert-butoxyoctyne are added to a Grignard solution prepared in a conventional manner from 51.1 g (2.1 moles) of magnesium and 228 g (2.1 moles) of ethyl bromide in 300 ml of tetrahydrofuran, the thoroughly stirred mixture is refluxed for 1 hour (the temperature increasing from 60° to 75° C.), 296 g (2 moles) of triethyl orthoformate are then added, and refluxing is continued until the conversion, determined by gas chromatography, is complete (about 15 hours). Thereafter, the mixture is poured into ice water, dissolved with ammonium chloride and extracted three times with methyl tert-butyl ether. Washing thoroughly and evaporating down give 555 g of a pale brown oil, which is shown by gas chromatography to contain 92% of 1,1-diethoxy-9-tert-butoxy-non-2-yne (corresponding to a yield of 91%).

(b) 940 g of crude, 71% strength 1,1-diethoxy-9-hydroxy-non-2-yne are initially taken together with 390 g of pyridine, and 502 g of acetic anhydride are added at from 60° to 70° C. The mixture is stirred for 4 hours at about 70° C. and then poured onto ice water, brought to pH 6 and extracted three times with methyl tert-butyl ether, and the extracts are washed with water and evaporated down. 1,160 g of 1,1-diethoxy-9-hydroxynon-2-yne are obtained. The yield after distillation (bp. 135°-137° C./0.4) is 650 g of 97% pure product, ie. 85% yield.

EXAMPLE 2

Apart from being obtained by reacting the octynol with the orthoester, the hydroxynonyne derivative used in the above Example can also be prepared from the tetrahydropyranyl derivative by elimination of the tetrahydropyranyl protective group; this possibility is surprising in that the diethoxynonyne tetrahydropyranyl ether used contains two acetal functions, of which only the tetrahydropyranyl function is selectively cleaved while the diethoxy function is retained.

1,230 g of 1,1-diethoxy-9-tetrahydropyranyloxy-non-2-yne in 5 l of ethanol are stirred with 25 g of p-toluenesulfonic acid for 20 hours at 20° C. and the mixture is then neutralized with sodium bicarbonate/$H_2O$, stirred into 5 l of $H_2O$ and extracted with methyl tert-butyl ether. Washing thoroughly with water and evaporating down gave 940 g of crude product (1,1-diethoxy-9-hydroxynon-2-yne). The content, determined by gas chromatography, is 70%; purification by distillation is not possible owing to the thermal instability, but the crude product can be used directly for stage (b) of Example 1 above.

The compounds below are prepared as described above, with appropriate modification:

| $R^1$ | $R^2$ | X | bp. [°C./mm Hg] | (O.Z. 0050/39371 270 MHz $^1$NMR δ [ppm] (CDCl$_3$) |
|---|---|---|---|---|
| $C_2H_5$ | $C_2H_5$ | (tetrahydropyranyl) | 165–168/0.4 | |
| $C_2H_5$ | $C_2H_5$ | tert-butyl | 134–136/0.7 | |
| $C_2H_5$ | $C_2H_5$ | H | | 1.1–1.6 (m, 14H), 2.23 (t, 2H), 3.6 (m, 6H), 5.22 (s, 1H) |
| $C_2H_5$ | $C_2H_5$ | COCH$_3$ | 135–137/0.4 | |
| $C_2H_5$ | $C_2H_5$ | CH(CH$_3$)OCH$_3$ | | |
| $C_2H_5$ | $C_2H_5$ | CH(CH$_3$)OCH$_2$CH$_3$ | | |
| $C_2H_5$ | $C_2H_5$ | CH(CH$_3$)OCH$_2$CH(CH$_3$)$_2$ | | |
| $C_2H_5$ | $C_2H_5$ | Si(CH$_3$)$_3$ | | |

| R¹ | R² | X | bp. [°C./mm Hg] | (O.Z. 0050/39371 270 MHz ¹NMR δ [ppm] (CDCl₃) |
|---|---|---|---|---|
| CH₃ | CH₃ | ![tetrahydropyranyl] | | |
| CH₃ | CH₃ | tert-butyl | | |
| CH₃ | CH₃ | H | | |
| CH₃ | CH₃ | COCH₃ | | |
| CH₃ | CH₃ | CH(CH₃)OCH₃ | | |
| CH₃ | CH₃ | CH(CH₃)OC₂H₅ | | |
| CH₃ | CH₃ | CH(CH₃)OCH₂CH(CH₃)₂ | | |
| CH₃ | CH₃ | Si(CH₃)₃ | | |

We claim:

1. A 1,1-dialkoxy- or 1,1-(α,ω-methylenedioxy)-non-2-yn-9-ol or its OH-protected derivative of the formula I

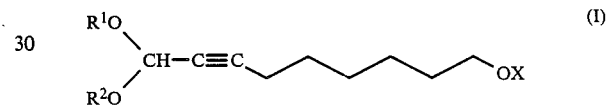

where R¹ and R² are each C₁–C₆-alkyl or together form an alkylene chain of 2 to 5 carbon atoms and X is hydrogen or a protective group which can be eliminated.

* * * * *

UNITED STATES PATENT AND TRADEMARK OFFICE
CERTIFICATE OF CORRECTION

PATENT NO.   : 4,877,891
DATED        : Oct. 31, 1989
INVENTOR(S)  : Rainer Becker, et al It is certified that error appears in the above-identified patent and that said Letters Patent is hereby corrected as shown below:

On the title page, item [75]:

The fourth inventor's last name is incorrect, "Brüchner" should be:

--Brueckner--

Signed and Sealed this

Twenty-fifth Day of December, 1990

*Attest:*

HARRY F. MANBECK, JR.

*Attesting Officer*    *Commissioner of Patents and Trademarks*